United States Patent

Vicari et al.

[11] Patent Number: 5,733,838
[45] Date of Patent: Mar. 31, 1998

[54] PROCESS FOR THE PRODUCTION OF A HYDROGENATION CATALYST

[75] Inventors: Maximilian Vicari, Neuhofen; Klemens Flick, Herxheim; Johann-Peter Melder, Mannheim; Werner Schnurr, Herxheim; Joachim Wulff-Döring, Frankenthal, all of Germany

[73] Assignee: BASF Aktiengesellschaft, Ludwigshafen, Germany

[21] Appl. No.: 767,382

[22] Filed: Dec. 16, 1996

Related U.S. Application Data

[63] Continuation of Ser. No. 375,572, Jan. 18, 1995, abandoned.

[51] Int. Cl.$^6$ .............. B01J 23/00; B01J 31/00; B01J 23/72; B01J 23/56
[52] U.S. Cl. .............. 502/335; 502/150; 502/156; 502/172; 502/301; 502/331; 502/337; 502/336; 502/346
[58] Field of Search .............. 502/156, 301, 502/331, 335, 336, 346

[56] References Cited

U.S. PATENT DOCUMENTS

| | | | |
|---|---|---|---|
| 2,865,865 | 12/1958 | Ockrent et al. | 252/430 |
| 3,966,645 | 6/1976 | Cairns et al. | 252/465 |
| 4,016,107 | 4/1977 | Sawyer et al. | 502/332 |
| 4,016,108 | 4/1977 | Robson | 502/332 |
| 4,048,196 | 9/1977 | Broecker et al. | 260/346.11 |
| 4,420,419 | 12/1983 | Ogawa et al. | 502/301 |
| 4,510,260 | 4/1985 | Stiefel et al. | 502/164 |
| 4,517,069 | 5/1985 | Harney et al. | 502/301 |
| 4,595,672 | 6/1986 | Ho et al. | 502/219 |
| 4,617,060 | 10/1986 | Dreibelbis | 106/214 |
| 4,709,118 | 11/1987 | Yan | 208/253 |
| 4,772,579 | 9/1988 | Thistlethwaite et al. | 502/338 |
| 4,783,435 | 11/1988 | Breibelbis | 502/214 |
| 4,794,098 | 12/1988 | Pohl et al. | 502/172 |
| 4,867,857 | 9/1989 | Von Benda et al. | 502/301 |
| 4,937,394 | 6/1990 | Dreibelbis | 568/896 |
| 5,063,189 | 11/1991 | Jowett | 502/301 |
| 5,380,179 | 1/1995 | Nishimura et al. | 419/36 |
| 5,536,694 | 7/1996 | Schuetz et al. | 502/301 |

FOREIGN PATENT DOCUMENTS

| | | | |
|---|---|---|---|
| 499534 | 1/1954 | Canada | 502/172 |
| 0 178 008 | 4/1986 | European Pat. Off. | 502/332 |
| 2159736 | 12/1971 | Germany . | |
| 161240 | 8/1985 | Germany | 502/332 |
| 2 079 170 | 1/1982 | United Kingdom | 502/172 |

OTHER PUBLICATIONS

Cheng et al., *Ind. Eng. Chem. Res.*, 1989, vol. 28, pp. 1764–1767.

*Primary Examiner*—Glenn Caldarola
*Assistant Examiner*—J. Pasterczyk

[57] ABSTRACT

A hydrogenation catalyst based on an alloy of aluminum and of a transition metal is prepared by preparing a kneaded material from the alloy and an assistant, converting the kneaded material into moldings, calcining the moldings and treating the calcined moldings with an alkali metal hydroxide, by a process in which the assistant used is (a) polyvinyl alcohol and water or
(b) stearic acid, and the catalyst prepared according to the invention is used for hydrogenation and hydrogenolysis, in particular the partial hydrogenation of aliphatic alpha,omega-dinitriles to aliphatic alpha,omega-aminonitriles.

9 Claims, No Drawings

PROCESS FOR THE PRODUCTION OF A HYDROGENATION CATALYST

This application is a continuation of application Ser. No. 08/375,572, filed on Jan. 18, 1995, now abandoned.

BACKGROUND OF THE INVENTION

The present invention relates to a process for the preparation of a hydrogenation catalyst based on an alloy of aluminum and of a transition metal by preparing a kneaded material from the alloy and an assistant, converting the kneaded material into moldings, calcining the moldings and treating the calcined moldings with an alkali metal hydroxide.

The present invention furthermore relates to processes for hydrogenation and hydrogenolysis, in particular the partial hydrogenation of aliphatic alpha,omega-dinitriles to aliphatic alpha, -omega-aminonitriles, and the use of the catalysts prepared according to the invention for hydrogenation and hydrogenolysis.

Ind. Eng. Chem. Res. 28 (1989), 1764–1767 describes a process for the preparation of catalysts of the Raney type. In this process, an alloy of aluminum and nickel is kneaded with polyethylene and mineral oil at 150° C. and then extruded to give moldings, after which the mineral oil is extracted with hexane. The moldings thus obtained are then calcined in air at from 900° to 1200° C., some of the aluminum being oxidized to alumina. The calcined moldings are converted into catalysts by treating said moldings with an alkali metal hydroxide, the major part of the unoxidized aluminum being dissolved out of the moldings. The disadvantage of this procedure is the use of relatively large amounts of mineral oil (20% by weight), which furthermore must be removed in a process step before the calcination with a further substance, the extracting agent hexane. Moreover, the temperature of 150° C. during kneading is too high for commercial applications owing to, inter alia, the energy consumption.

SUMMARY OF THE INVENTION

It is an object of the present invention to provide a process which does not have the stated disadvantages. In particular, it is intended to simplify the process compared with the prior art by dispensing with the need for an intermediate step for removing the assistant.

We have found that this object is achieved by an improved process for the preparation of a hydrogenation catalyst based on an alloy of aluminum and a transition metal for preparing a kneaded material from the alloy and an assistant, converting the kneaded material into moldings and calcining the moldings and treating the calcined moldings with an alkali metal hydroxide, wherein the assistant used is (a) polyvinyl alcohol and water or (b) stearic acid.

We have also found processes for hydrogenation and hydrogenolysis, in particular the partial hydrogenation of aliphatic alpha,omega-dinitriles to aliphatic alpha,omega-aminonitriles, and the use of the catalysts prepared according to the invention for hydrogenation and hydrogenolysis.

In the novel process, a kneaded material is first prepared from an alloy of aluminum and of a transition metal and an assistant.

The transition metals used may be preferably nickel, cobalt, iron and copper, particularly preferably nickel and cobalt.

The aluminum alloy is prepared in a manner known per se, for example by the process described in DE-A 21 59 736.

The weight ratio of aluminum to transition metal in the alloy is chosen to be as a rule from 35:1 to 80:1, preferably from 50:1 to 70:1.

The assistant used according to the invention is either (a) polyvinyl alcohol and water or (b) stearic acid.

Polyvinyl alcohol having a molecular weight of from 3000 to 6000, preferably from 4500 to 5500, g/mol is usually used.

The weight ratio of polyvinyl alcohol to water is chosen in general to be from 0.3:1 to 0.4:1, preferably from 0.35:1 to 0.37:1. Observations to date have shown that, outside this range, the kneaded material can be processed to moldings only with difficulty, if at all.

DESCRIPTION OF THE PREFERRED EMBODIMENTS

In a preferred embodiment, the alloy is first mixed with the usually solid polyvinyl alcohol and water is then added a little at a time until a readily moldable, plastic kneaded material is obtained.

When polyvinyl alcohol and water are used as the assistant, the weight ratio of assistant to alloy is chosen to be, as a rule, from 4:1 to 23:1, preferably from 13:1 to 19:1, the preparation of the kneaded material usually being carried out at from 10° to 40° C., preferably from 25° to 35° C.

The weight ratio of stearic acid to alloy is usually chosen to be from 0.01:1 to 1.0:1, preferably from 0.04:1 to 0.06:1, the preparation of the kneaded material usually being carried out at from 70° to 140° C., preferably from 75° to 85° C.

The kneaded material can be prepared in a manner known per se, for example in an appropriate mixing or kneading apparatus.

According to the invention, moldings are produced from the kneaded material comprising essentially alloy and assistant. Observations to date have shown that the three-dimensional shape of the moldings and their production are not critical for the success of the invention. Preferred moldings are, for example, pellets and extrudates. The moldings are usually processed in apparatuses known for this purpose, for example in extruders or pelleting machines.

In the case of processing in extruders, an L/D ratio of from 10:1 to 2:1, preferably from 3:1 to 5:1, a temperature of from 10° to 40° C., preferably from 25° to 35° C., and a pressure of from 10 to 20, preferably from 12.5 to 17.5, MPa are usually chosen.

In a particular embodiment, extrudates having a diameter of 1.5 mm and a length of 5 mm are produced, the production being carried out, as a rule, in such a way that, immediately after emerging from the extruder, the resulting extrudates are subjected to a temperature of from 100° to 200° C for from 0.2 to 2 minutes for superficial drying. Drying is then effected for 12 hours at 120° C.

The moldings are usually calcined at from 700° to 1200° C., preferably from 750° to 900° C., the residence time being, as a rule, from 0.5 to 3, preferably from 0.9 to 1.1, hours. In a particular embodiment, the moldings are first heated for one hour at 750° C. and and [sic] the temperature is then increased to 900° C. for two hours.

The calcination is usually carried out in air at atmospheric pressure.

According to the invention, the calcined moldings are activated with an alkali metal hydroxide, such as lithium hydroxide, sodium hydroxide, potassium hydroxide or cesium hydroxide, preferably sodium hydroxide, or a mixture thereof. As a rule, an aqueous solution of the alkali metal hydroxide, in particular sodium hydroxide solution, is used, the weight ratio of water to alkali metal hydroxide generally being from 10:1 to 30:1, preferably from 15:1 to 25:1. The molar ratio of alkali metal hydroxide to aluminum is chosen to be, as a rule, from 1:1 to 4:1, preferably from 1.5:1 to 2.5:1. The temperature of the activation is usually chosen to be from 25° to 95° C., preferably from 45° to 80° C. The duration of the activation depends essentially on the desired final aluminum content and is usually from 10° to 30, preferably from 15 to 25, hours. Advantageously, the activation is monitored by measuring the amount of hydrogen liberated during the activation.

After the activation, the activated and calcined moldings are usually washed with water, preferably until the pH of the wash water is at least 8.0, and moldings are kept under water, preferably in a mixture of water and methanol.

The catalysts prepared according to the invention can be used for hydrogenation and hydrogenolysis, for example for the hydrogenation of C—C and C—N double and triple bonds, and of ketones and alcohols, for ether cleavage, for the reduction of nitro compounds and oximes, for the preparation of secondary amines from ketones and primary amines, for dehalogenation and for the reduction of thioketones.

In a preferred embodiment, the catalysts according to the invention are used for the partial hydrogenation of aliphatic alpha,omega-dinitriles to aliphatic alpha,omega-aminonitriles.

The partial hydrogenation can be carried out either in the gas phase or in the liquid phase, in a tube reactor, either by the liquid phase procedure or by the trickle-bed procedure, preferably the latter.

Aliphatic alpha,omega-dinitriles of the general formula I

NC—(CH$_2$)$_n$—CN    I where n is an integer from 1 to 10, in particular 2, 3, 4, 5 or 6, may be used as starting materials. Particularly preferred compounds I are succinonitrile, glutaronitrile, adiponitrile, pimelonitrile and suberonitrile, very particularly preferably adiponitrile. In the preferred process, the dinitriles I described above are partially hydrogenated in the presence of a solvent using the catalyst prepared according to the invention to give alpha,omega-aminonitriles of the general formula II

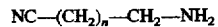

NC—(CH$_2$)$_n$—CH$_2$—NH$_2$    II where n has the abovementioned meanings. Particularly preferred aminonitriles II are those in which n is 2, 3, 4, 5 or 6, in particular 4, ie. 4-aminobutyronitrile, 5-aminopentanenitrile, 6-aminohexanenitrile (6-aminocapronitrile), 7-aminoheptanenitrile and 8-aminooctanenitrile, very particularly preferably 6-aminocapronitrile.

The partial hydrogenation in the liquid phase is preferably carried out at from 20° to 150° C., preferably from 30° to 90° C., and, as a rule, at from 2 to 30, preferably from 3 to 20, MPa. The partial hydrogenation is particularly preferably carried out in the presence of a solvent, preferably ammonia, amines, diamines and triamines and triamines of 1 to 6 carbon atoms, such as trimethylamine, triethylamine, tripropylamine or tributylamine, or alcohols, such as methanol and ethanol, particularly preferably ammonia. In a preferred embodiment, an ammonia content from 1 to 10, preferably from 2 to 6, g per g of adiponitrile is chosen. A catalyst space velocity of from 0.1 to 2.0, preferably from 0.3 to 1.0, kg of adiponitrile per 1 per h is preferably chosen. Here too, the conversion and hence the selectivity can be controlled by changing the residence time.

In the partial hydrogenation in the gas phase, a catalyst space velocity of from 0.03 to 10, preferably from 0.05 to 3, kg of dinitrile per kg of catalyst per hour is generally maintained.

The hydrogen concentration in the inlet gas usually depends on the dinitrile concentration. The molar ratio of hydrogen to dinitrile is as a rule from 2:1 to 300:1, preferably from 10:1 to 200:1.

The gas-phase reaction can be carried out in the presence or absence of a solvent, continuously as a fixed-bed reaction with a fixed catalyst, for example by the liquid phase or trickle-bed procedure, or as a fluidized-bed reaction using catalyst fluidized upward and downward. The fixed-bed procedure is preferred. By changing the residence time, the conversion and hence the selectivity can be controlled.

In the partial hydrogenation in the gas phase, temperatures of from 100° to 250° C., preferably from 150° to 220° C., in particular from 160° to 200° C., and pressures of from 0.1 to 30, preferably from 0.7 to 10, particularly preferably from 0.9 to 5, bar are usually used.

In the preferred process, alpha,omega-aminonitriles are obtained in in [sic] good selectivities and with only small amounts of hexamethylenediamine. Furthermore, the catalysts used according to the invention have a substantially longer life than comparable prior art catalysts. The alpha, omega-aminonitriles are important starting compounds for the preparation of cyclic lactams, in particular 6-aminocapronitrile for caprolactam.

The advantages of the novel process are that it is simpler and consumes less energy compared with prior art processes.

EXAMPLES

Example 1

Preparation of an aluminum/nickel catalyst 90 ml of water were added a little at a time to a mixture of 800 g of a powder consisting of an alloy of 48% by weight of nickel and 52% by weight of aluminum (prepared similarly to Example 1 in DE-A 21 59 736) and 33 g of a polyvinyl alcohol (molecular weight=5000 g/mol), and the mixture was then kneaded for three hours in a kneader. The resulting kneaded material was then processed in an extruder at 15 MPa and room temperature to give extrudates having a thickness of 1.5 mm and a length of 5 mm. The extrudates obtained were superficially dried at 120° C. for 2 minutes and then kept at 120° C. for 012 [sic] hours. The calcination was carried out first at 750° C for one hour and then at 900° C. for two hours.

For activation, 1.5 l of a 20% strength by weight NaOH solution were added at 90° C. to 500 g of the extrudates thus prepared. After 26 hours (the resulting amount of hydrogen was 143.2 l), the extrudates were washed with water, the pH of the final wash water being 7.5.

Example 2

Preparation of pellets containing stearic acid as an assistant 2250 g of an Al/Ni alloy powder (the powder used was the same as that in Example 1) was heated to 80° C. and mixed with 112.5 g of liquid stearic acid. After cooling, the resulting solid material was forced through a sieve having a mesh size of 1 mm to give a powder. This powder was pelleted (3 mm diameter, 3 mm height) at room temperature on a pelleting machine.

The pellets thus obtained were calcined for two hours at 900° C. For activation, 1.5 l of a 20% strength by weight sodium hydroxide solution were added at 90° C. to 411 g of the pellets. After 24 hours, the pellets were cooled and were washed with water for 30 hours (the pH of the final wash water was 8.0).

Example 3
Partial hydrogenation

A mixture of 55 ml/h of adiponitrile, 120 ml/h of liquid ammonia and 200 l/h [lacuna] was passed, at 18 MPa and 35° C., through a reactor having a length of 55 cm and an internal diameter of 1.5 cm and containing 80 ml (156 g) of the catalyst obtained in Example 1.

At a conversion of 56%, the reaction mixture was composed of 44% by weight of adiponitrile, 44% by weight of 6-aminocapronitrile and 12% by weight of hexamethylenediamine. When the temperature was increased to 40° C., the conversion increased to 68%. The reaction mixture was composed of 32% by weight of adiponitrile, 50% by weight of 6-aminocapronitrile and 17% by weight of hexamethylenediamine.

Example 4
Gas-phase hydrogenation

Adiponitrile and hydrogen were passed, at a reaction temperature of 180° C. and a hydrogen/adiponitrile molar ratio of 50:1, over 100 ml of the catalyst from Example 1 by the trickle-bed procedure, the catalyst space velocity being 0.15 g of ADN per g of catalyst per hour. the [sic] gaseous reacted mixture was condensed in cold traps and was analyzed by gas chromatography. The 6-aminocapronitrile yield was 53% (selectivity 72%, conversion 74%) and the HMD yield was 6%.

We claim:

1. A process for preparing a hydrogenation catalyst, said catalyst comprising an alloy of aluminum and a transition metal, said process comprising preparing a kneaded material from the alloy and an assistant, converting the kneaded material into moldings, calcining the moldings and treating the calcined moldings with an alkali metal hydroxide, wherein the assistant used is (a) polyvinyl alcohol and water or (b) stearic acid.

2. A process as defined in claim 1, wherein the transition metal used is nickel, cobalt, iron or copper.

3. A process as defined in claim 1 or 2, wherein the kneaded material is prepared at from 70 to 140° C.

4. A process as defined in claim 1, wherein the assistant is not removed before the calcination.

5. A process as defined in claim 1, wherein the weight ratio of polyvinyl alcohol to water is chosen to be from 0.3:1 to 0.4:1.

6. A process as defined in claim 1, wherein the weight ratio of alloy to polyvinyl alcohol is chosen to be from 20:1 to 80:1.

7. A process as defined in claim 1, wherein the polyvinyl alcohol has a molecular weight of from 3000 to 6000 g/mol.

8. The process of claim 1, wherein the transition metal used is nickel, cobalt or copper;

the kneaded material is prepared at a temperature of from 70 to 140° C.;

the assistant is not removed before the calcination;

the weight ratio of polyvinyl alcohol to water is from 0.3:1 to 0.4:1;

the weight ratio of alloy to polyvinyl alcohol to water is from 20:1 to 80:1; and the polyvinyl alcohol has a molecular weight of from 3000 to 6000 g/mol.

9. The method of claim 8 wherein the kneaded material is prepared at a temperature of from 75 to 85° C.

\* \* \* \* \*

UNITED STATES PATENT AND TRADEMARK OFFICE
CERTIFICATE OF CORRECTION

PATENT NO.: 5,733,838

DATED: March 31, 1998

INVENTOR(S): VICARI et al.

It is certified that error appears in the above-identified patent and that said Letters Patent is hereby corrected as shown below:

On the title page, insert item:

--[30] Foreign Application Priority Data

Dec. 27, 1994 [DE] Germany ................. P 44 46 907.1--.

Signed and Sealed this

Third Day of November, 1998

Attest:

BRUCE LEHMAN

Attesting Officer

Commissioner of Patents and Trademarks